(12) United States Patent
Abbate et al.

(10) Patent No.: US 8,241,554 B1
(45) Date of Patent: Aug. 14, 2012

(54) METHOD OF FORMING A STENT PATTERN ON A TUBE

(75) Inventors: Anthony J. Abbate, Santa Clara, CA (US); David C. Gale, San Jose, CA (US); Klaus Kleine, Los Gatos, CA (US); Svava Maria Atladottir, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1371 days.

(21) Appl. No.: 10/881,554

(22) Filed: Jun. 29, 2004

(51) Int. Cl.
*B29D 22/00* (2006.01)
(52) U.S. Cl. ........................................................ 264/573
(58) Field of Classification Search .................. 148/593; 623/1.15; 264/573
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |

(Continued)

FOREIGN PATENT DOCUMENTS

DE 44 07 079 9/1994
(Continued)

OTHER PUBLICATIONS

U.S. Appl. No. 10/317,435, filed Dec. 11, 2002, Hossainy et al.
(Continued)

*Primary Examiner* — Larry Thrower
(74) *Attorney, Agent, or Firm* — Squire Sanders (US) LLP

(57) ABSTRACT

Methods of fabricating an implantable medical device from a tube or a sheet in an expanded or stretched state, respectively, are disclosed herein. The implantable medical device may be an endoprosthesis such as a stent. In one embodiment, the method may include radially expanding a tube about a cylindrical axis of the tube from a first diameter to a second diameter. The method may further include forming a pattern on at least a portion of the expanded tube. Additional embodiments may include forming a stent pattern on a stretched sheet from which a stent may be formed. In addition, a stent pattern may be formed on a tube that is formed from a stretched sheet.

4 Claims, 5 Drawing Sheets

U.S. PATENT DOCUMENTS

| | | |
|---|---|---|
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,957,687 A * | 9/1990 | Akman et al. ............. 264/506 |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,500,013 A * | 3/1996 | Buscemi et al. ............. 623/1.22 |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,891,386 A * | 4/1999 | Deitermann et al. ......... 264/526 |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |

| | | |
|---|---|---|
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0028241 A1* | 2/2003 | Stinson ............... 623/1.15 |
| 2003/0033001 A1 | 2/2003 | Igaki |
| 2003/0083732 A1* | 5/2003 | Stinson ............... 623/1.15 |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1* | 12/2003 | Shapovalov et al. ...... 219/121.72 |
| 2003/0236565 A1 | 12/2003 | Fifer |
| 2004/0000361 A1* | 1/2004 | Trozera ............... 148/593 |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Weber |
| 2004/0143317 A1 | 7/2004 | Stinson et al. |
| 2004/0167610 A1 | 8/2004 | Fleming, III |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |

| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64 (1984).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovscular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-l-Lactic Acid Coronary Stents in Humans*, Circulation, pp. 399-404 (2000).

Tsui et al., *Biodegradable Polymeric Stents*, Current Interventional Cardiology Reports 3, pp. 10-17 (2001).

Völkel et al., *Targeting of immunoliposomes to endothelial cells using a single—chain Fv fragment directed against human endoglin (CD105)*, Biochemica et Biophysica Acta 1663, pp. 158-166 (2004).

Yau et al. Modern Size-Exclusion Liquid Chromatography, Wiley-Interscience Publication, (1979).

\* cited by examiner

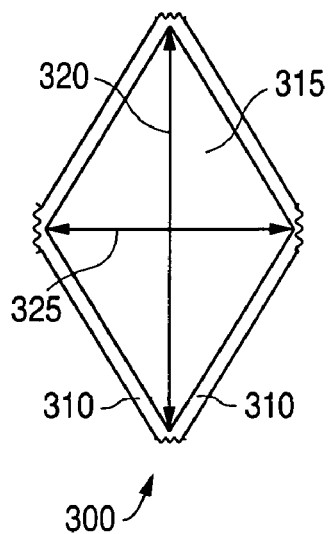
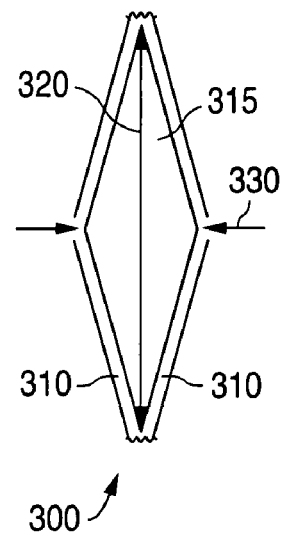
FIG. 8A    FIG. 8B
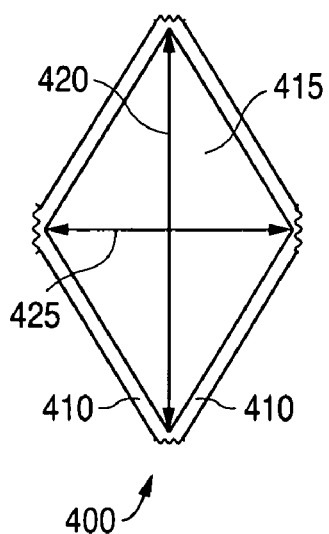
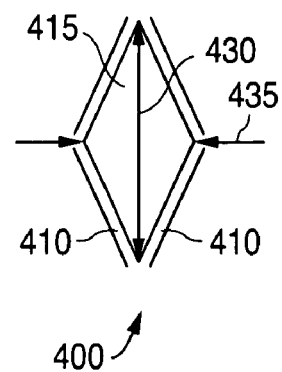
FIG. 9A    FIG. 9B

METHOD OF FORMING A STENT PATTERN ON A TUBE

BACKGROUND OF THE INVENTION

1. Field of the Invention

This invention relates to a method of fabricating implantable medical devices such as stents.

2. Description of the State of the Art

This invention relates to radially expandable endoprostheses which are adapted to be implanted in a bodily lumen. An "endoprosthesis" corresponds to an artificial device that is placed inside the body. A "lumen" refers to a cavity of a tubular organ such as a blood vessel. A stent is an example of these endoprostheses. Stents are generally cylindrically-shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

A treatment involving a stent involves both delivery and deployment of the stent. "Delivery" refers to introducing and transporting the stent through a bodily lumen to a region requiring treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. The stent is then expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

Stents have been made of many materials such as metals and plastic, including biodegradable plastic materials. Stents have been formed from wire, tube stock, etc. Stents have also been made from sheets of material which are rolled into a cylindrical shape. The structure of a stent is typically composed of a pattern that allows the stent to be radially expandable. The pattern should be designed to maintain the longitudinal flexibility and radial rigidity required of the stent. Longitudinal flexibility facilitates delivery of the stent and radial rigidity is needed to hold open a bodily lumen.

A number of techniques have been suggested for the fabrication of stents from polymer and metal sheets and tubes. One such technique involves laser cutting or etching a pattern onto a material. Laser cutting may be performed on a sheet of material which is then rolled into a tube. Alternatively, a desired pattern may be formed directly onto a tube. Other techniques involve cutting a desired pattern onto a sheet or a tube via chemical etching or electrical discharge machining. Laser cutting of stents has been described in a number of publications including U.S. Pat. No. 5,780,807 to Saunders, U.S. Pat. No. 5,922,005 to Richter, and U.S. Pat. No. 5,906,759 to Richter.

Laser cutting techniques applied to forming patterns for stents have certain shortcomings. For instance, laser cutting a desired pattern onto a tube or sheet can be limited by the kerf width of the laser, the width of a cut made by a laser beam on a material. For example, the kerf width of a laser may make it difficult to cut a desired fine, intricate pattern onto a tube or a sheet. Therefore, methods that address this shortcoming of laser cutting techniques are desirable.

SUMMARY OF THE INVENTION

The present invention is directed to a method for fabricating an implantable medical device such as a stent from a tube or sheet in a deformed state. In one embodiment, the method may include radially expanding a tube about a cylindrical axis of the tube from a first diameter to a second diameter. The method may further include forming a pattern on at least a portion of the expanded tube.

An additional embodiment of the invention may include stretching a sheet along an axis of stretching from a first length to a second length. The method may further include forming a pattern on at least a portion of the stretched sheet. A tube may then be formed from the stretched sheet with the pattern. In another embodiment, a tube may be formed from the stretched sheet prior to forming a pattern. The method may further include forming a pattern on at least a portion of the tube.

BRIEF DESCRIPTION OF THE DRAWINGS

FIGS. 8A-B and 9A-B depict examples of portions of stent patterns.

DETAILED DESCRIPTION OF THE INVENTION

Figure 1:
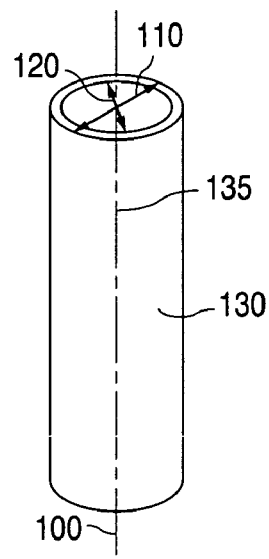
FIG. 1 depicts a conduit or tube.

For the purposes of the present invention, the following terms and definitions apply:

"Delivery diameter" refers to a diameter at which a cylindrical or substantially cylindrical implantable medical device, such as a stent, is introduced into and transported through a bodily lumen.

"Deployment diameter" refers to a diameter which a cylindrical or substantially cylindrical implantable medical device, such as a stent, is expanded to within a bodily lumen.

The "glass transition temperature," $T_g$, is the temperature at which the amorphous domains of a polymer change from a brittle vitreous state to a solid deformable state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

The "melting temperature", $T_m$, of a polymer is the highest temperature at which a crystal lattice in the polymer is stable. The $T_m$ of a polymer is also known as the fusion temperature ($T_f$). The $T_m$ is always greater than the $T_g$ for a given polymer.

The term "elastic deformation" refers to deformation of a body in which the applied stress is small enough so that the object retains, substantially retains, or moves towards its original dimensions once the stress is released. However, an elastically deformed polymer material may be prevented from returning to or moving towards an undeformed state if the material is cooled below the $T_g$ of the polymer. Below the $T_g$, energy barriers may inhibit or prevent molecular movement that allows deformation or bulk relaxation.

The term "plastic deformation" refers to permanent deformation that occurs in a material under stress after elastic limits have been exceeded.

The term "implantable medical device" is intended to include self-expandable stents, balloon-expandable stents, stent-grafts, and grafts. The structural pattern of the device can be of virtually any design. The device can also be made partially or completely from a biodegradable, bioabsorbable, or biostable polymer. The polymer may also be purified.

Polymers can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded, absorbed, and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. For stents made from a biodegradable polymer, the stent is intended to remain in the body for a duration of time until its intended function of, for example, maintaining vascular patency, and/or drug delivery is accomplished.

Representative examples of polymers that may be used to fabricate an implantable medical device using the methods disclosed herein include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

In some embodiments, an implantable medical device may be fabricated from a conduit or tube. The tube may be cylindrical or substantially cylindrical in shape. For example, FIG. 1 depicts a tube 100. Tube 100 has an outside diameter 110 and an inside diameter 120. FIG. 1 also depicts a surface 130 and a cylindrical axis 135 of tube 100. When referred to below; the "diameter" of the tube refers to the outside diameter of tube. In some embodiments, the diameter of the tube prior to fabrication of the implantable medical device may be between about 0.1 mm and about 30 mm. In other embodiments, the diameter of the tube prior to fabrication may be between about 1 mm and about 3 mm.

Figure 2:
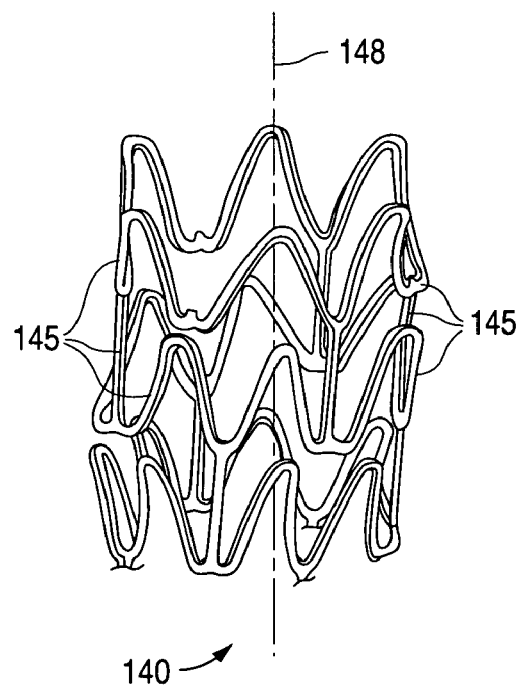
FIG. 2 depicts an example of a stent with a pattern.

FIG. 2 depicts an example of a three-dimensional view of a stent 140 formed from a tube using a cutting or etching process. The pattern may include a number of interconnecting elements or struts 145. The implantable medical device may have a cylindrical axis 148. The final cut out pattern should not be limited to what has been illustrated as other stent patterns are easily applicable with the method of the invention.

Figure 3A:
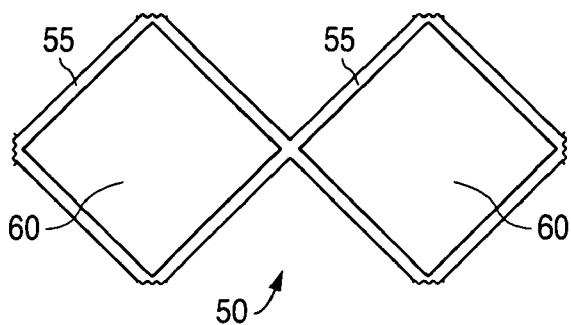
FIGS. 3A and 3B depict examples of portions of stent patterns.
Figure 3B:
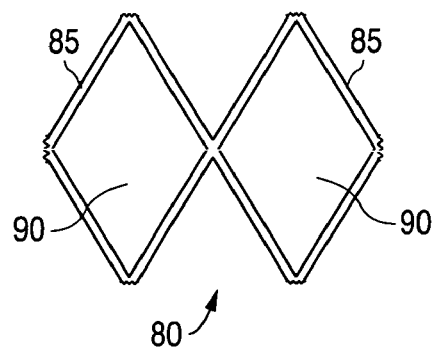

Typically, stent patterns as shown in FIG. 2 are formed on tubes or sheets using a laser cutting process. Representative examples of laser techniques that may be used include excimer, carbon dioxide, and YAG. In other embodiments, chemical etching may be used to form a pattern on the expanded tube. It is desirable to use a laser cutting technique in a manner that minimizes a size of a heat affected zone. A heat affected zone refers to a region of a target material affected by the heat of the laser. Heat from the laser may melt at least a portion of polymer in the heat affected zone. As indicated above, a potential shortcoming of laser cutting techniques is that the kerf width of the laser may be too wide to permit cutting of intricate patterns. Patterns that include fine, intricate designs that require cutting portions that are in close proximity are particularly difficult to cut. Such patterns may be more desirable for cutting stents that are close to a crimping diameter. As a pattern becomes more fine and intricate, the greater the chance that heat affected zones may overlap which may lead to breaks in a pattern. For example, FIGS. 3A and 3B illustrate two examples of stent patterns. FIG. 3A depicts a portion 50 of a stent pattern with struts 55 and cut-out regions 60. FIG. 3B depicts a portion 80 of a stent pattern with struts 85 and cut-out regions 90. The pattern in FIG. 3B is finer and more intricate than the pattern in FIG. 3B, and therefore, may be more difficult to cut with a laser.

The difficulty faced in forming fine, intricate patterns may be addressed by forming a stent pattern on a tube in an expanded or deformed state. The tube may then be reduced to a size less than its expanded state or to a size the same as or generally equivalent to the initial state. Certain embodiments of fabricating an implantable medical device may include radially expanding a tube about a cylindrical axis of the tube from a first diameter to a second diameter. The tube may be expanded radially by application of a radial pressure. The first diameter may correspond to a diameter of the tube prior to fabrication of the implantable medical device. In addition, the second diameter may refer to a diameter of the tube in an expanded state. In certain embodiments, expanding the tube may facilitate forming a desired pattern in the tube. The method may further include forming a pattern on at least a portion of the expanded tube. During formation of the pattern, it may be desirable to maintain the tube at or near the expanded state. In some embodiments, expansion, forming the pattern, and/or allowing the tube to reduce to a smaller size may be performed in a temperature range equal to or above the $T_g$ and below the melting temperature of a polymer of the tube. In other embodiments, the temperature range may be less than the $T_g$ of the polymer. It may be advantageous to expand the tube elastically to facilitate the return of the expanded tube to or approximately to its original dimensions. In other embodiments, expansion may include plastic deformation of the tube.

In some embodiments, the first diameter may be equal to or less than a deployment diameter of the implantable medical device and equal to or greater than a delivery diameter of the implantable medical device. In other embodiments, the first diameter may be less or equal to a delivery diameter of the implantable medical device. In an embodiment, the second diameter may be equal to or greater than the deployment diameter of the implantable medical device. In other embodiments, second diameter may be equal to or greater than the delivery diameter and equal to or less than the deployment diameter. In some embodiments, the second diameter may be up to 500% of the first diameter, such as from 101% of the first diameter to 200% of the first diameter. In other embodiments, the second diameter may be between about 150% and about 300% of the first diameter.

Additionally, expansion of the tube may be facilitated by applying heat. Increasing the temperature of a polymer tends to allow a polymer to be deformed more easily. For instance, it may be desirable to increase the temperature to at or above the $T_g$, but below the melting temperature of the polymer, $T_m$. In various embodiments, the application of heat may be prior to, contemporaneous with, and/or subsequent to expansion. In some embodiments, heat may be applied by contacting the tube with a fluid above ambient temperature. An ambient temperature may be about 25° C. For example, the tube may be immersed in a liquid and/or contacted with a stream of gas. The tube may be translated through the liquid and/or the stream of gas. In addition, the tube may be heated through contact and/or close proximity to a heated object. In another embodiment, heat may be applied by using an oven. In other embodiments, the expansion of the tube may be performed satisfactorily without application of heat. For example, a polymer with a $T_g$ below an ambient temperature may deform adequately to a desired expanded state without application of heat.

In some embodiments, radial pressure may be applied to the polymer tube by positioning the polymer tube within an annular member and conveying a gas at a selected pressure into a proximate end of the polymer tube. A distal end of the polymer tube may be closed. Subsequent processing steps may be used to open the distal end. The annular member may act to control the diameter of the expanded polymer tube by limiting the expansion to the inside diameter of the annular member. The inside diameter of the annular member may correspond to a desired diameter of the polymer tube. Alternatively, the pressure of the conveyed gas may be used to control the expansion of the polymer tube to a desired diameter.

Figure 4A:
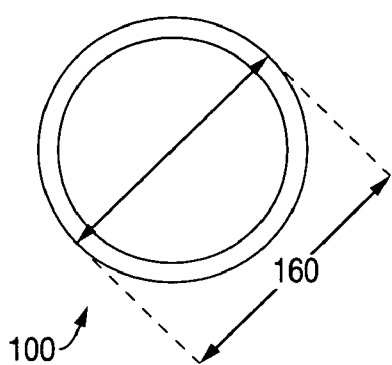
FIGS. 4A and 4B depict radial cross-sections of a tube.
Figure 4B:
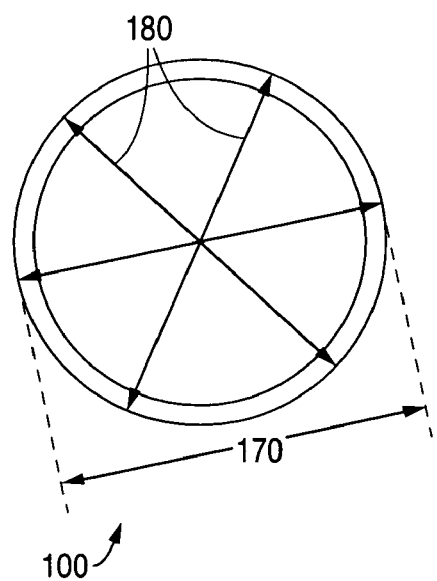
Figure 5A:
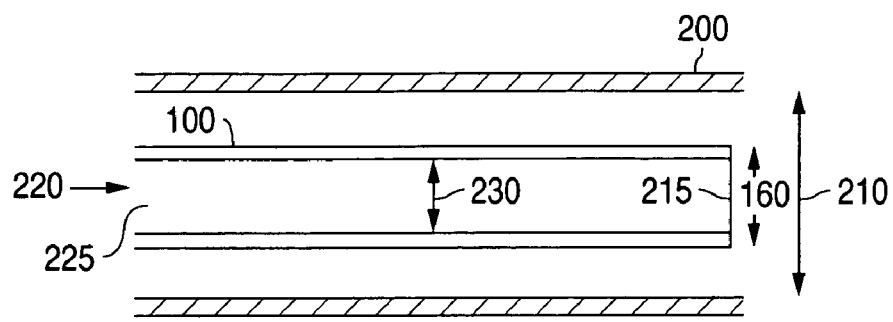
FIGS. 5A and 5B depict a method of expanding a tube.
Figure 5B:
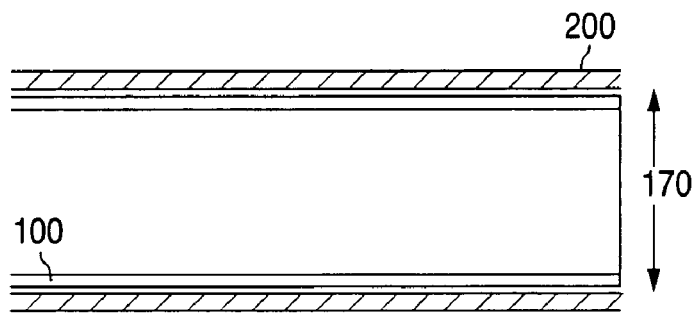

FIG. 4A depicts a radial cross-section of tube 100 from FIG. 1 and FIG. 4B depicts a radial cross-section of tube 100 in an expanded state. Tube 100 has a first diameter 160. In FIG. 4B, the arrows 180 illustrate the outward radial pressure applied to expand tube 100 from first diameter 160 to a second diameter 170. Various embodiments of the method may include different degrees of expansion of the tube. In addition, FIGS. 5A and 5B illustrate a method of expanding a polymer tube for use in fabricating an implantable medical device. FIG. 5A depicts an axial cross-section of tube 100 with an outside diameter 160 positioned within an annular member 200. Annular member 200 may act as a mold that limits the expansion of tube 100 to a diameter 210, the inside diameter of annular member 200. Tube 100 may be closed at a distal end 215. A gas, such air or an inert gas such as nitrogen, argon, etc., may be conveyed, as indicated by an arrow 220, into an open proximate end 225 of tube 100. Tube 100 may be heated by heating the gas to a temperature above ambient temperature prior to conveying the gas into tube 100. Alternatively, heat may be applied to the exterior of annular member 200. The conveyed gas combined with the applied heat may act to radially expand tube 100, as indicated by an arrow 230. FIG. 5B depicts tube 100 in an expanded state with an outside diameter 170 within annular member 200.

Furthermore, due to heating of the tube, the temperature of the tube during and/or after expansion may be higher than an ambient temperature. Heating may be from applying heat to the tube and/or from the forming the pattern. As indicated above, an elastically deformed polymer material above the $T_g$ of the material tends to relax towards its undeformed state when stress is removed. Several embodiments of the method may include inhibiting or preventing relaxation of the expanded tube prior to and during forming the pattern onto the expanded tube. The tendency to relax may increase as the temperature increases. In one embodiment, radial pressure may be applied or maintained during the forming of the pattern. Applying radial pressure may include conveying a gas into the expanded tube. Additionally, applying radial pressure may include supporting the expanded tube, for example, by positioning the expanded tube over an annular member, such as a mandrel, to inhibit or prevent relaxation of the expanded tube. Some embodiments may include applying heat to the tube during the forming of the pattern.

In some embodiments, it may be desirable to cool the expanded tube. In certain embodiments, it may be desirable to inhibit or prevent relaxation of the expanded tube towards its unexpanded state. Cooling the expanded tube may stabilize the tube in an expanded state. During or after expansion, the tube may be at a first temperature, which may be above the $T_g$ of the polymer. As indicated above, below the $T_g$ energy barriers preventing movement of polymer molecules may inhibit or prevent even an elastically deformed material from returning to its unstressed state. Therefore, cooling the tube to a temperature below $T_g$ may stabilize the tube in an expanded state. In some embodiments, a method may include decreasing the temperature of the tube from a first temperature to a second temperature prior to, contemporaneous with, and/or subsequent to forming the pattern. In some embodiments, the second temperature may be below the $T_g$ of the polymer. In other embodiments, the second temperature may be above $T_g$, but low enough that the polymer does not relax significantly during the time frame of the forming process.

Some embodiments of the method may include decreasing the temperature of the tube relatively slowly in a temperature range at or near an ambient temperature. One embodiment may include contacting the tube with a fluid, for example, a stream of an inert gas such as air, nitrogen, etc. If the tube is cooled prior to forming the pattern, it may be necessary to apply radial pressure to the tube to inhibit relaxation during the cooling process.

Alternatively, if the tube is cooled subsequent to forming the pattern, it may be desirable to allow relaxation of the tube towards it original diameter. If such is the case, then the tube may be cooled without applying radial pressure. However, the tube may stabilize at or less than or equal to $T_g$ prior to reaching its original unexpanded state.

In other embodiments, the tube may be cooled relatively quickly or by a fast quench from a first temperature to a second temperature. In an embodiment, the expanded tube may be contacted with a fluid below an ambient temperature and/or below the $T_g$ of the polymer. For example, refrigerated air cooled by liquid nitrogen or by some other means may be blown onto the expanded tube. Radial pressure may be applied to inhibit or prevent relaxation of the polymer.

Additionally, after forming a pattern, a tube may be stable in an expanded state at a diameter greater than a desired diameter. It may be desirable to decrease the diameter of the expanded tube close to a delivery or crimped diameter. The tube may have been stabilized in an expanded state by cooling the tube, as described above. Alternatively, the expanded tube may be above $T_g$, and it may be desirable to speed up the relaxation towards the unexpanded, relaxed state. Relaxation of the expanded tube may be facilitated by heat shrinking the tube. Increasing a temperature of an elastically deformed material facilitates relaxation to an unstressed state. Some embodiments of the method may include increasing a temperature of the expanded tube to a temperature in a manner that decreases a diameter of the tube to a third diameter. In one embodiment, the third diameter may be approximately equal to the first diameter or original diameter. Alternatively, the third diameter may be less the second diameter and greater than the first diameter. In some embodiments, the third diameter may be less than the first diameter.

Additionally, various embodiments may be distinguished by the relative size of the third diameter relative to the delivery diameter of the medical device. In some embodiments, the third diameter may be greater than or equal to the delivery diameter. In other embodiments, the third diameter may be less than the delivery diameter. When the third diameter is greater than a delivery diameter, a method of fabricating an implantable medical device may further include decreasing the diameter of the tube to a delivery diameter. Decreasing the diameter of the tube may be accomplished by crimping the tube.

Further embodiments of addressing the difficulty of forming fine, intricate patterns may include forming a stent pattern on a stretched or deformed sheet from which a stent may be formed. A stent pattern may also be formed on a tube formed from a stretched or deformed sheet. A stretched sheet or tube formed from a stretched sheet may be relaxed at least partially from a stretched or deformed state.

Certain embodiments of fabricating an implantable medical device may include stretching a sheet along an axis of stretching from a first length to a second length. The sheet may be stretched by application of a tensile force. The first length may correspond to an initial state of the sheet prior to fabrication of the device. In addition, the second length may be the length of the sheet in a stretched or deformed state. In some embodiments, the second length may be up to 500% of the first length, such as from 101% of the first length to 200% of the first length. In other embodiments, the second length may be between about 150% and about 300% of the first length. Stretching the sheet may facilitate forming a desired pattern on the sheet or a tube formed from a stretched sheet.

In certain embodiments, the method may include forming a pattern on at least a portion of the stretched sheet after stretching the sheet. The method may further include forming a tube from the stretched sheet. A cylindrical axis of the tube may be parallel, perpendicular, or at an angle between parallel and perpendicular to the axis of stretching. In an embodiment, the method may include forming a pattern on the formed tube. The formed tube may then be allowed to relax or reduce to a smaller diameter. The stretched sheet with the pattern may also be allowed to relax prior to forming the tube.

In other embodiments, the method may include forming the tube from the stretched sheet prior to forming a pattern. A pattern may then be formed on at least a portion of the tube that is in an expanded or stretched state due to stretching of the sheet. The formed tube may then be allowed to reduce or relax to a smaller size. The pattern on a stretched sheet or formed tube may be formed using a laser cutting technique or chemical etching.

Certain embodiments may include stretching the sheet along a second axis of stretching. A cylindrical axis of the tube may be parallel, perpendicular, or at an angle between parallel and perpendicular to the second axis of stretching.

Figure 6:
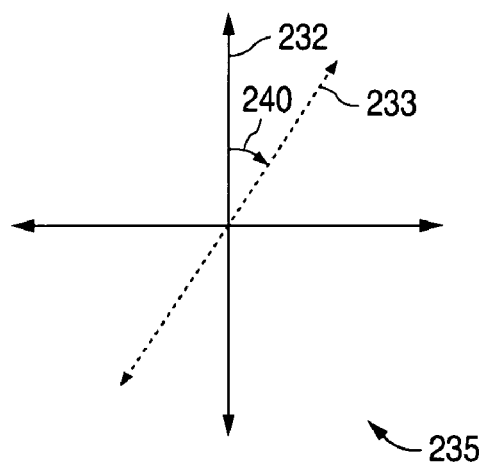
FIG. 6 depicts an x-y coordinate plane.

In certain embodiments, a tube may be formed from a sheet by rolling a sheet into a cylindrical shape. The sheet may then be bonded with a suitable adhesive at the opposing edges of the sheet that are parallel or substantially parallel to a cylindrical axis. The sheet may be cut so that the formed tube is a desired diameter. FIG. 6 depicts an x-y coordinate plane 235 for illustrating the relationship between an axis of stretching 232 and a cylindrical axis 233 of a tube formed from a sheet. A tube may be formed from a stretched sheet at an orientation 240.

Figure 7A:
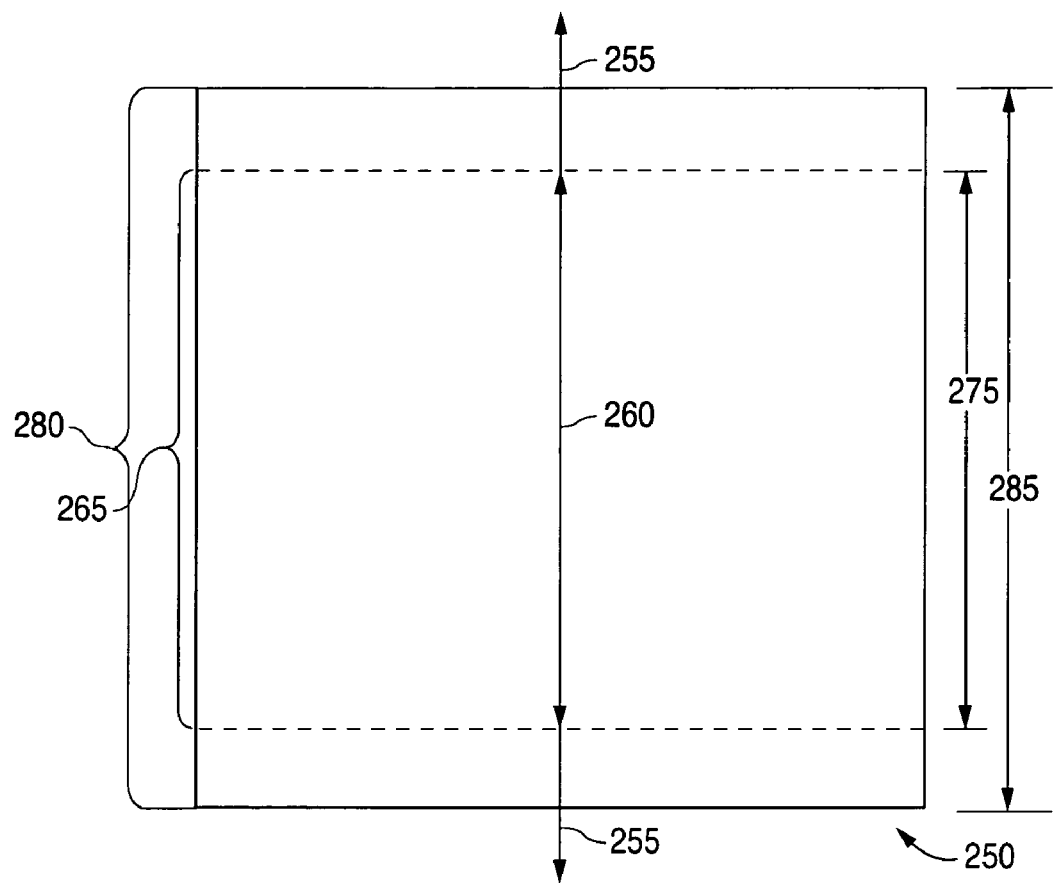
FIG. 7A depicts stretching a sheet.
Figure 7B:
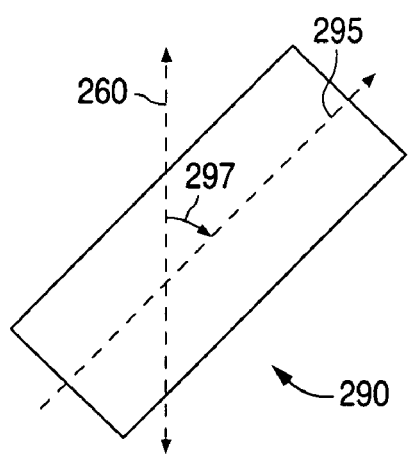
FIG. 7B depicts a tube.

FIG. 7A depicts stretching of a sheet 250 with a tensile force 255. Sheet 250 may be stretched or elongated along an axis 260 parallel to tensile force 255. Tensile force 255 may cause sheet 250 to stretch along axis of stretching 260. An unstretched sheet 265 depicts the configuration of sheet 250 prior to stretching and a stretched sheet 280 depicts the configuration of sheet 250 subsequent to stretching. A length 275 of sheet 265 and a length 285 of sheet 280 are depicted. In some embodiments, tensile force 255 and the resultant stretching of sheet 250 may cause a decrease in a width and/or thickness of sheet 250. FIG. 7B depicts a projection of a tube 290 formed from sheet 250 after stretching. Tube 290 has a cylindrical axis 295 which is at an orientation 297 relative to axis of stretching 260.

During formation of the pattern on a formed tube or stretched sheet, it may be desirable to maintain the formed tube or the stretched sheet at or near the expanded or stretched state. In some embodiments, stretching, forming the pattern, and/or allowing the formed tube or stretched sheet to relax or reduce to a smaller size may be performed in a temperature range equal to or above the $T_g$ and below the melting temperature of a polymer of the sheet or tube. It may be advantageous to stretch the sheet elastically to facilitate the relaxation of the stretched sheet or tube formed from a stretched sheet towards an undeformed state. In other embodiments, the sheet may be expanded plastically.

Additionally, as in expansion of a tube, stretching may be facilitated by applying heat. In various embodiments, the application of heat may be prior to, contemporaneous with, and/or subsequent to stretching. Heat may be applied in ways similar to that described above.

In one embodiment, a sheet may be stretched along at least one an axis using a tenter. In a tenter, stretching is performed inside of a box that may be temperature-controlled. Inside of the box, a sheet may be grasped on either side by tenterhooks that exert a tensile force or drawing tension along at least one axis.

In addition, the temperature of the sheet during and/or after expansion and the tube after it is formed may be higher than an ambient temperature due to heating and/or forming the pattern. Several embodiments of the method may include inhibiting or preventing relaxation of the stretched sheet or formed tube prior to and during forming the pattern onto the stretched sheet or formed tube. In an embodiment, a tensile force may be applied to or maintained on the sheet during the forming of the pattern. Radial pressure may be applied to the formed tube as describe above. Some embodiments may include applying heat to the stretched sheet or formed tube during the forming of the pattern.

Furthermore, it may be desirable to cool the stretched sheet or the formed tube to inhibit or prevent relaxation of the stretched sheet or formed tube prior to and during forming a pattern on the stretched sheet or formed tube. Cooling the stretched sheet or the formed tube may stabilize the stretched sheet or formed tube in a stretched state or expanded state. The stretched sheet or formed tube may be cooled in manners similar to that described above.

If the stretched sheet or the formed tube is cooled prior to forming the pattern, it may be necessary to apply a tensile force or radial pressure, respectively, to inhibit relaxation during the cooling process. Alternatively, if the stretched sheet or the formed tube is cooled subsequent to forming the pattern, it may be desirable to allow relaxation of the stretched sheet or the formed tube. If such is the case, then the stretched tube or formed tube may be cooled without applying tensile force or radial pressure, respectively. However, the stretched sheet or the formed tube may stabilize at or less than or equal to $T_g$ of the polymer prior to reaching an undeformed state. In other embodiments, the stretched sheet or the formed tube may be cooled relatively quickly or by a fast quench from a first temperature to a second temperature.

Additionally, after forming a pattern, a stretched sheet or formed tube may be stabilized in a deformed state. It may be desirable to relax the stretched sheet with a pattern to inhibit or prevent undesirable changes in dimensions of a tube formed from the stretched tube with a pattern during any subsequent processing steps of the device or during use of the device. As described above, relaxation may be facilitated by heat shrinking the stretched sheet with a pattern or the formed tube with a pattern. In some embodiments, the stretched sheet may be relaxed to a third length by increasing a temperature of the stretched tube. In one embodiment, the third length may be less than or equal to the first length. Alternatively, the third length may be less the second length and greater than the first length. A tube with a pattern, or stent, with a desired diameter may then be formed from a stretched sheet with a pattern after heat shrinking. A desired diameter may be greater than a deployment diameter; less than or equal to a deployment diameter and greater than or equal to a delivery diameter; or less than a delivery diameter.

Alternatively, a tube may be formed from a stretched sheet with a pattern while still in a stretched or deformed state. As discussed above, it may be desirable to relax the formed tube to decrease its diameter close to a delivery or crimped diameter. The formed tube may be subjected to heat shrinking as described above. The diameter of the formed tube may be decreased, for example, to greater than or equal to a deployment diameter; to less than or equal to a deployment diameter and greater than or equal to a delivery diameter; or to less than or equal to a delivery diameter. For a tube that has a diameter greater than a delivery diameter, a method of fabricating an implantable medical device may further include decreasing the diameter of the formed tube to a delivery diameter. Decreasing the diameter of the tube may be accomplished by crimping the tube.

Furthermore, forming a pattern in an expanded state may result in a desired fine, intricate pattern on a stent. The diameter of the stent may close to the crimped state. It may not be possible to form such a pattern with laser cutting. Furthermore, crimping tends to result in a nonuniform change in the geometry of a stent pattern. However, heat shrinking an expanded tube with a pattern, a tube with a pattern formed from a stretched sheet, or a stretched sheet with a pattern may result in a relatively uniform change in the geometry of the stent. Therefore, forming a pattern on tubes or sheets in expanded or stretched states may allow better control over the geometry of a stent pattern.

FIGS. 8A-B and 9A-B illustrate the influence of forming a stent pattern on a tube in an expanded state. FIGS. 8A and 8B depict a portion 300 of a pattern on a stent that was formed on a tube or sheet that was not in an expanded or stretched state. FIG. 8A depicts portion 300 prior to crimping of the stent. Portion 300 includes struts 310 and a cut-out region 315 that was removed by cutting. Region 315 has dimensions 320 and 325. FIG. 8B depicts portion 300 after crimping of the stent. After crimping, dimension 320 is substantially unchanged, however, dimension 325 decreases to a dimension 330.

FIGS. 9A and 9B depict a portion 400 of a pattern on a stent that was formed on a tube or sheet that was in an expanded or stretched state. FIG. 9A depicts portion 400 prior to heat shrinking the stent from the expanded state with the same diameter as the stent in FIG. 8A. Portion 400 includes struts 410 and a cut-out region 415 that was removed by cutting. Region 415 has dimensions 420 and 425. FIG. 9B depicts portion 400 after heat shrinking the stent. After heat shrinking, region 415 has decreased in size relatively uniformly. Dimension 420 has decreased to a dimension 430 and dimension 425 has decreased to a dimension 435. Therefore, forming a pattern on a tube in an expanded state or a sheet in a stretched state allows formation of a more uniform and intricate pattern.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a medical device including a stent crimped to a balloon, the stent having a first diameter when crimped to the balloon, comprising the following sequential steps:

providing a cutting tool for forming a pattern in a polymer tube, the pattern being characterized by struts and a cut-out region separating the struts, the cut-out region being characterized by a circumferential length and longitudinal length, wherein the pattern is such that when formed in the tube and the tube is crimped from a second diameter to the first diameter a non-uniform decrease of the cut-out region occurs, whereby a non-uniform decrease is such that the circumferential length decreases by a lesser or greater degree than the longitudinal length relative to their respective lengths before crimping from the second diameter to the first diameter;

forming the tube including radially expanding the tube to the second diameter;

forming the pattern in the tube when the tube has the second diameter, followed by heat shrinking the tube to a third diameter, less than the second diameter, wherein the cut-out region decreases more uniformly when the heat shrunk tube is crimped from the third diameter to the first diameter than if the tube was crimped from the second diameter to the first diameter; and crimping the heat-shrunk tube from the third diameter to the first diameter, thereby fabricating the medical device.

2. The method of claim 1, wherein the tube comprises a polymer, and wherein the temperature of the tube during expansion and forming is less than a melting temperature of the polymer.

3. The method of claim 1, wherein the temperature of the tube during an expansion to the second diameter is equal to or greater than a glass transition temperature of the polymer.

4. The method of claim 1, wherein the second diameter is less than or equal to a deployment diameter.

* * * * *